(12) United States Patent
Krüger et al.

(10) Patent No.: US 10,821,246 B2
(45) Date of Patent: Nov. 3, 2020

(54) MEDICAL DEVICE AND METHOD FOR DETERMINING OPERATING SITUATIONS IN A MEDICAL DEVICE

(71) Applicant: Drägerwerk AG & Co. KGaA, Lübeck (DE)

(72) Inventors: Thomas Krüger, Reinfeld (DE); Birger Landwehr, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 227 days.

(21) Appl. No.: 15/804,245

(22) Filed: Nov. 6, 2017

(65) Prior Publication Data

US 2018/0126103 A1 May 10, 2018

(30) Foreign Application Priority Data

Nov. 7, 2016 (DE) .................. 10 2016 013 138

(51) Int. Cl.
*A61M 16/00* (2006.01)
*A61M 16/12* (2006.01)
(Continued)

(52) U.S. Cl.
CPC ...... *A61M 16/024* (2017.08); *A61M 16/0003* (2014.02); *A61M 16/0051* (2013.01);
(Continued)

(58) Field of Classification Search
CPC .. A61M 16/00; A61M 16/021; A61M 16/022; A61M 16/024; A61M 16/0003;
(Continued)

(56) References Cited

U.S. PATENT DOCUMENTS 2,904,035 A 9/1959 Andreasen
5,400,777 A 3/1995 Olsson et al.
(Continued)

FOREIGN PATENT DOCUMENTS

EP 0444243 A2 * 9/1991 .......... A61B 5/0873
WO 2007/085110 A1 8/2007
(Continued)

OTHER PUBLICATIONS

Willburta Q. Lindh, Marilyn Pooler, Carol D. Tamparo, Barbara M. Dahl, "Delmar's Comprehensive Medical Assisting: Administrative and Clinical COmpetencies", Mar. 16, 2009, Cengage Learning, p. 573 (Year: 2009).*

(Continued)

*Primary Examiner* — Samchuan C Yao
*Assistant Examiner* — Vincent D Hoang
(74) *Attorney, Agent, or Firm* — McGlew and Tuttle, P.C.

(57) ABSTRACT

A medical device determines operating situations and a method determines operating situations in a medical device. Based on pressure measured values (99) and flow measured values (97), it is determined whether an elevation of an airway pressure (105) in a medical device is due to a cough event (113) or to a plurality of cough events (117), which indicate an accumulation of secretion. An outputting (41, 42, 44) of a warning (44) or alarm (41, 42) is provided indicating the accumulation of secretion.

20 Claims, 2 Drawing Sheets

(51) Int. Cl.
*A61M 16/20* (2006.01)
*A61M 16/01* (2006.01)
*A61M 16/04* (2006.01)
*A61M 16/08* (2006.01)
*A61B 5/00* (2006.01)
*A61B 5/091* (2006.01)
*A61B 5/08* (2006.01)
*A61B 5/087* (2006.01)

(52) U.S. Cl.
CPC .......... *A61M 16/01* (2013.01); *A61M 16/04* (2013.01); *A61M 16/0875* (2013.01); *A61M 16/12* (2013.01); *A61M 16/205* (2014.02); *A61B 5/087* (2013.01); *A61B 5/0816* (2013.01); *A61B 5/091* (2013.01); *A61B 5/746* (2013.01); *A61M 2016/0027* (2013.01); *A61M 2016/0036* (2013.01); *A61M 2016/0039* (2013.01); *A61M 2016/0042* (2013.01); *A61M 2202/0208* (2013.01); *A61M 2205/18* (2013.01); *A61M 2205/3553* (2013.01); *A61M 2205/3561* (2013.01); *A61M 2205/3584* (2013.01); *A61M 2205/3592* (2013.01); *A61M 2205/505* (2013.01); *A61M 2205/581* (2013.01); *A61M 2205/583* (2013.01)

(58) Field of Classification Search
CPC .. A61M 16/0051; A61M 16/01; A61M 16/02; A61M 16/04; A61M 16/0875; A61M 16/205; A61M 2016/0027; A61M 2016/0039; A61M 2016/0042; A61M 2016/0015; A61M 2016/0018; A61M 2016/0021; A61M 2016/0024; A61M 2016/003; A61M 2016/0033; A61M 2016/0036; A61M 2205/18; A61M 2205/581; A61M 2205/583; A61M 2205/13; A61M 2205/14; A61M 2205/186; A61M 2205/3331; A61M 2205/3334; A61M 2205/3351; A61M 2205/3355; A61M 2202/0208; A61M 2210/1025; A61M 2230/40; A61B 5/742; A61B 5/746; A61B 5/0816; A61B 5/087; A61B 5/091

See application file for complete search history.

(56) References Cited

U.S. PATENT DOCUMENTS

| | | |
|---|---|---|
| 5,606,968 A | 3/1997 | Mang |
| 5,937,853 A | 8/1999 | Ström |
| 6,553,990 B2 | 4/2003 | Hoffmann |
| 6,571,792 B1 | 6/2003 | Hendrickson et al. |
| 8,483,831 B1 * | 7/2013 | Hlavka .................. A61B 5/686 607/42 |
| 2008/0275349 A1 * | 11/2008 | Halperin ................ A61B 5/447 600/484 |
| 2011/0197885 A1 * | 8/2011 | Wondka ................ A61B 5/087 128/204.22 |
| 2014/0150795 A1 * | 6/2014 | Milne ............... A61M 16/0057 128/205.23 |
| 2017/0127977 A1 * | 5/2017 | Weffers-Albu ...... A61B 5/1128 |
| 2018/0035901 A1 * | 2/2018 | Cronin ............... A61B 5/02438 |
| 2018/0133418 A1 * | 5/2018 | Brand ................ A61M 16/202 |
| 2018/0243521 A1 * | 8/2018 | Lee ...................... A61B 5/0823 |

FOREIGN PATENT DOCUMENTS

| | | | |
|---|---|---|---|
| WO | 2008/098382 A1 | 8/2008 | |
| WO | WO-2013042071 A1 * | 3/2013 | ........... A61B 5/0823 |
| WO | 2015/007373 A1 | 1/2015 | |
| WO | WO-2017032882 A1 * | 3/2017 | ........ A61M 16/0051 |

OTHER PUBLICATIONS

Respiratory Care, Oct. 2008, vol. 53, No. 10.
Stegmaier, Peter A. et al.—Fuzzy Logic Cough Detection: A First Step Towards Clinical Application.

* cited by examiner

MEDICAL DEVICE AND METHOD FOR DETERMINING OPERATING SITUATIONS IN A MEDICAL DEVICE

CROSS REFERENCE TO RELATED APPLICATIONS

This application claims the benefit of priority under 35 U.S.C. § 119 of German Application DE 10 2016 013 138.1, filed Nov. 7, 2016, the entire contents of which are incorporated herein by reference.

FIELD OF THE INVENTION

The present invention pertains to a medical device with a determination of operating situations, as well as to a method for determining operating situations in a medical device.

BACKGROUND OF THE INVENTION

The medical device may be configured as an anesthesia apparatus, as a ventilator (also known as a medical respirator) for adult patients or children, as an emergency respirator for use in rescue or search operations on land, on water or in the air, or as a special, so-called neonatal ventilator for ventilating newborns. Medical devices for ventilating a patient are known from the state of the art. For example, there are the above-mentioned ventilators, emergency respirators, neonatal ventilators as well as anesthesia apparatuses, which make it possible to ventilate patients mechanically, in a mandatory or assisted manner. Ventilators are preferably used on intensive care units for treating patients in whom the possibility of supplying with breathing air and oxygen as well as of removing carbon dioxide by the patient's spontaneous breathing activity is minimized or limited.

Ventilators for carrying out mechanical ventilation according to the state of the art are described in U.S. Pat. Nos. 2,904,035, 5,400,777, 5,937,853, and WO 2007/085110 A1.

Anesthesia apparatuses are used during the duration of a surgery in order to supply the patient with anesthetics, so that an anesthetizing effect can be achieved on the patient. In addition, the anesthesia apparatus also assumes the mechanical ventilation of the patient, because the patient is no longer able to have spontaneous breathing activity due to the anesthetizing action.

Anesthesia apparatuses for carrying out anesthesia in humans or animals according to the state of the art are described in WO 2008/098382 A1, U.S. Pat. Nos. 6,571,792 and 6,553,990.

Inadmissible operating states must be avoided for the operation of ventilators, and operating situations that could lead to inadmissible operating states must be detected as early as possible and as quickly as possible in order to avoid the possible onset of or longer-lasting inadmissible operating states.

A method for alarm organization in a medical device, for example, in an anesthesia apparatus or ventilator, as well as a medical device with an alarm organization during the ventilation of a patient are known from the application filed by the applicant on Jun. 16, 2016 and with the application No. 10 2016 007 336.5. It is described in this application how the alarm is generated by the medical device in case of a detected individual cough event for an alarm that indicates an elevated airway pressure, in agreement with the ISO 80601-2-12 standard, in a different manner than in case of another state of the medical device.

Concerning the subject of elevations of the airway pressure $P_{AW}$ and its measurement, the possible causes of cough events as well as concerning the possibilities of detecting and determining individual cough events and concerning the sensor system described there for pneumatic/fluidic physical states such as pressure and flow rates and the measuring sites suitable for the sensor system, this patent application 10 2016 007 336.5 shall be considered to have been included in this specification with its disclosure content by means of this reference.

The principal relationships, situations and causes necessary for understanding, in which elevations of the airway pressure may be given, shall therefore be listed here only briefly. For further details, reference should be made to the application filed by the applicant on Jun. 16, 2016 with application No. 10 2016 007 336.5 (corresponding U.S. patent application Ser. No. 15/623,815, filed Jun. 15, 2017, is hereby incorporated by reference in its entirety)

Disturbances in the dispensing of breathing gas in the medical device:
   Disturbances in the flow/volume or pressure regulation are possible causes of elevations of the airway pressure. Such disturbances may be caused, for example, by mechanical or pneumatic components, such as valves or dispensing units, which have a malfunction.

Blockages in the gas supply:
   Another cause of an elevation of the airway pressure may be a compromise in the gas-carrying components. Blockages in the gas-carrying components, for example, ventilation tubes, may hinder the supply and/or removal of breathing air to or from the patient. For example, a constriction or kink in the line leading away from the patient may thus lead to the build-up of an elevated pressure in front of the kink point.

Accumulations of condensation:
   Similarly to how kink points in the tube affect the pressure conditions in the tube or at the patient, accumulations of water, which may be formed due to condensation of the humidified breathing air as well as of the moist exhaled air in the tube, may also have such an effect that an elevation of the airway pressure is possible.

Accumulations of secretion:
   Another possibility for an elevation of the airway pressure is a possible occlusion of an endotracheal tube used for ventilation, which is inserted into the trachea of the patient via the oral cavity. One possibility for an occlusion of the endotracheal tube arises from accumulations of secretion, the so-called mucus, in the endotracheal tube. Such accumulations increase the flow resistance in the endotracheal tube and thus lead to an elevation of the pressure. A secretion or an accumulation of secretion or sputum in the airways, which is partially removed from the airways by the patient with the exhalation or by means of coughing, is called mucus. For example, shortness of breath and irritation of the throat may be triggered by an accumulation of secretion or mucus in the patient. The irritation of the throat is usually present as long as the situation in which secretion or mucus accumulates is present and comes to an end, as a rule, when the patient has succeeded in ejecting the secretion by means of coughing.

Counter exhalation:
Another possibility for elevations of the airway pressure arises from situations with a so-called counter exhalation (counter breathing) by the patient. Counter exhalation designates the state in which the medical device for carrying out the mechanical ventilation delivers air to or into the patient, but the patient is attempting to exhale at the same time, i.e., to counter exhale. In this case, the patient and the ventilator are not synchronous with one another during the inspiratory phases (inhalation) and exhalation. Such a state is rather stressful for the patient, and such a state should therefore be avoided as much as possible.

User interactions:
Other causes for elevations of the airway pressure are setting actions performed by the user, for example, in case of changes in limit values, changes in pressure and volume values. Such user interactions may lead to pressure changes and hence to elevations of the airway pressure.

Cough events:
Cough events may also be triggered by the fact that accumulations of secretion in the airways or in regions of the lungs or of the bronchi trigger an irritation of the throat of the patient. Such an irritation of the throat or even a cough reflex is independent from whether the current phase of ventilation is an inspiratory phase (inhalation) or an expiratory phase (exhalation), and in any case it is an event during which an additional quantity of exhaled breathing gas enters the tube system with the cough abruptly, quasi as a pulse, and an increased flow rate will thus flow away from the patient. This pulse-like increase in the flow rate leads as a consequence to a massive increase in pressure or a transient pressure event for a brief time.

Messages, warnings and alarms play a major role for guaranteeing the health and safety of the patient in clinical practice during the operation of medical devices such as ventilators or anesthesia apparatuses. Thus, possibly occurring critical operating situations can be monitored by monitoring physical or physiological variables such as pressure ($P_{insp}$, $P_{exp}$, PEEP), volume ($V_t$, RMV), flow rates, temperatures, gas concentrations ($O_2$, $CO_2$) by means of defined limit values or threshold values.

The accumulation of secretion, the so-called mucus, in the airways (trachea, bronchi) as well as in regions of the lungs of a patient is a special context of an operating situation during the operation of the medical device, which may lead to critical operating situations. It is seen in WO 2015 007 373 A1 that the settings of the ventilator affect not only the gas exchange itself, but they may also affect the transport of the secretion. Accumulation of secretion may occur now in the lungs of a patient. The fundamental effect of ventilation settings on the transport of secretion is described in the medical clinical literature, such as in Respiratory Care, October 2008, Vol. 53, No. 10. A wide variety of ventilation settings such as respiration rate (RR), inspiration time to expiration time ratio (I:E ratio), inspiratory pressure and pressure curve, end-expiratory pressure (PEEP), expiratory pressure and pressure curve, flow upper limits, pressure upper limits, respiratory minute volume (RMV), are usually coupled with ventilation modes and are provided in different forms of "pressure-controlled" and "volume-controlled" ventilation modes of medical devices for performing the ventilation.

The breathing air present in the lungs is exchanged during the ventilation cyclically in the rhythm of a respiration rate. In addition to the breathing gases, secretion is additionally present in the bronchial region (trachea, bronchi) and partly also in the upper regions of the lungs of a patient. This secretion, the so-called mucus, is removed, as a rule, during a spontaneous breathing activity by the normal natural exhalation from the lungs and from the bronchial tract.

This removal from the lungs and the bronchial tract is usually supported by additional reactions of a patient, which are caused by irritations, such as coughing or sneezing.

During mechanical ventilation by a ventilator, the patient is ventilated, as a rule, by means of a pneumatic/fluidic port in the form of an endotracheal tube or a nasal mask. The endotracheal tube or the nasal mask is joined by a ventilation tube or a ventilation tube system to an air- and gas-carrying connection to the ventilator. During mechanical ventilation, the breathing of a patient, i.e., the alternation between inhalation and exhalation, is preset by settings on the ventilator essentially mandatorily, i.e., in a forcibly actuated and automated manner.

A problem that arises in this connection is that the supply and removal of breathing gases by means of the pneumatic/fluidic port are adversely affected by accumulations of secretion or sputum. In addition, accumulations of secretion or sputum trigger, as a rule, an irritation of the throat of the patient, which is explained by the circumstance that the secretion in itself as well as together with the endotracheal tube is perceived by the patient as a foreign body, which at least partly blocks the free permeability of the trachea. This problem is typically solved in routine clinical practice by the secretion being aspirated in an automated manner by the ventilator itself or by an auxiliary unit connected to the ventilator. As an alternative, a so-called secretion aspiration is performed by the clinical staff at regular intervals within the framework of a usual routine clinical practice, wherein the patient is briefly disconnected from the ventilator, i.e., the air- or gas-carrying connection between the ventilator and the patient is interrupted and the secretion is aspirated from the lungs via the endotracheal tube by means of a secretion aspirator.

Such a secretion aspirator is shown in U.S. Pat. No. 5,606,968.

The usual routine clinical practice is based essentially on empirical values. The aspiration of secretions is carried out in routine clinical practice at time intervals, which are based on the clinical procedure and not always on the individual needs of the plurality of patients and the quantities of secretion actually present in their airways.

In most cases, the situation of secretion aspiration represents both an uncomfortable, at times painful procedure, which does, however, always compromise the constitution and the general well-being. In addition, the disconnected patient cannot be ventilated for a short time for the duration of the aspiration. From this arises the need for minimizing the frequency of secretion aspiration in routine clinical practice to the extent possible in order to be make the ventilation as comfortable for the patient as possible.

SUMMARY OF THE INVENTION

From this arises an object of the present invention to provide a medical device in which operating situations of the medical device concerning disturbances in the supply and removal of breathing gases are determined.

Another object of the present invention is to provide a method for determining operating situations of a medical device concerning disturbances in the supply and removal of breathing gases.

According to the invention, a method for determining operating situations is provided. The method is provided with a medical device configured for processing sensor signals of the medical device, which are provided by sensors wherein sensor signals indicate pneumatic/fluidic physical states of a breathing gas in a connection system connected and coupled in a gas-carrying manner with the anesthesia apparatus or ventilator and configured for transporting gases from and to a patient, from which values of an airway pressure and of a flow rate as well as of the flow rate in the gas-carrying connection system are determined in flow directions belonging to the gas-carrying connection system. The method comprises detecting pneumatic/fluidic physical states in the gas-carrying connection system with a determination of values of pressure and flow rates, comparing the determined values of the airway pressure to a comparison criterion to determine whether the comparison criterion is exceeded by a currently determined value of the airway pressure and determining whether the medical device is in an operating state in which a smaller quantity of breathing gas is fed by the medical device to the patient than flows away from the patient on the basis of a comparison to determine whether the determined value of the flow rate and the determined flow direction of flow exceed a comparison criterion indicating a flow rate and a flow direction. The method further provides for checking to determine whether a cough event or a plurality of cough events has/have occurred during a checking time interval since a chronologically preceding checking time and initializing the checking time interval and beginning of a detection, counting and recording of a number of cough events with an initial cough event. If at least one cough event has not occurred during the checking time interval since the chronologically preceding checking time and if the medical device is currently in an operating state in which a smaller quantity of breathing gas is fed by the medical device to the patient than flows away from the patient and if the comparison criterion indicating the airway pressure is exceeded by the currently determined value of the airway pressure, the method provides for continuing of the checking to determine, counting and recording of the number of cough events. If at least one cough event has occurred during the checking time interval since the chronologically preceding checking time and if the medical device is currently in the operating state in which a smaller quantity of breathing gas is fed by the medical device to the patient than flows away from the patient and if the comparison criterion indicating the airway pressure is exceeded by the currently determined value of the airway pressure the method provides a comparing of the number of cough events detected during the checking time interval with a predefined comparison number, determining, on the basis of the comparison of the detected number of cough events to the predefined comparison number, whether an operating situation that indicates an accumulation of fluid is present, and providing a control signal that indicates the operating situation in which accumulation of secretion occurs.

According to another aspect of the invention, a medical device is provided comprising a connection system configured for transporting breathing gas, the connection system comprising an expiratory path configured and intended for removing an expiratory quantity of breathing gas from the patient, an inspiratory path configured and intended for feeding an inspiratory quantity of breathing gas from the medical device to the patient, a patient connection path configured and intended for feeding an inspiratory quantity of breathing gas from the medical device to the patient and to remove the expiratory quantity of breathing gas from the patient, wherein the expiratory path and the inspiratory path are connected to one another and to the patient connection path by a connection component, a control unit, a pressure-measuring unit comprising at least one pressure sensor arranged in or at the medical device or the connection system and is configured and is intended for detecting a measured value of a pressure, which is prevailing in the connection system, and wherein the pressure-measuring unit is configured to provide this at least one pressure measured value to the control unit as an airway pressure and a flow-measuring unit comprising at least one flow sensor arranged in or at the connection system or in or at the medical device and is configured and is intended for detecting at least one flow rate measured value of a quantity of breathing gas and a flow direction of the breathing gas, which flow direction is associated to the flow rate measured value, which said quantity flows away from the patient in the connection system or flows from the medical device towards the patient, and wherein the flow-measuring unit is configured to provide this at least one flow rate measured value and the corresponding flow direction to the control unit. An alarm generation unit is also provided. The control unit is configured: to determine or input at least one pressure measured value; to determine a current airway pressure on the basis of the at least one pressure measured value; to make a comparison on the basis of the determined values of the airway pressure to determine whether a comparison criterion indicating the airway pressure is exceeded by the currently determined value of the airway pressure; to determine or input at least one flow measured value; to determine whether the medical device is in an operating state in which a smaller quantity of breathing air is fed by the medical device to the patient than flows away from the patient on the basis of information from the course of the ventilation and/or from information concerning a state of an expiratory valve or an actuating signal for such an expiratory valve, and/or on the basis of a comparison performed to determine whether a comparison criterion indicating a flow rate and a flow direction is exceeded by the determined value of the flow rate and by the determined flow direction; to check whether a cough event or a plurality of cough events has/have occurred during a checking time interval since a chronologically preceding checking time; to initialize the checking time interval and beginning of a detection and counting and recording of a number of cough events if at least one cough event has not occurred during the checking time interval since the chronologically preceding checking time and if the medical device is currently in the operating state in which a smaller quantity of breathing air is fed by the medical device to the patient than flows away from the patient, and the comparison criterion indicating the airway pressure is exceeded by the currently determined value of the airway pressure; to continue the detection, counting and recording of the number of cough events if at least one cough event has occurred during the checking time interval since the chronologically preceding checking time and if the medical device is currently in the operating state in which a smaller quantity of breathing gas is fed by the medical device to the patient than flows away from the patient and if the comparison criterion indicating the airway pressure is exceeded by the currently determined value of the airway pressure; to compare the number of cough events detected during the checking time interval with a predefined comparison number; to determine, on the basis of the comparison concerning the detected number of cough events in relation to the predefined comparison number, an operating situation that indicates an accumulation of secretion is present; and to provide a control signal which indicates the operating situation with accumulation of secretion.

Provisions are made according to the present invention in a medical device, which is suitable for ventilating a patient or living beings and is configured to use existing measured values, signals of sensors, also called sensor signals, to detect whether an operating situation with disturbances in the supply and in the removal of breathing gases from the airways of a patient is present.

The medical device on which the method for determining operating situations is carried out is preferably configured as an anesthesia apparatus or as a ventilator, especially as a ventilator suitable for long-term ventilation for use on an intensive care unit of a hospital.

Disturbances in the supply and in the removal of breathing gases from the airways of a patient arise at the pneumatic/fluidic port, i.e., in the endotracheal tube or at the transition of the endotracheal tube due to accumulations of viscous liquids, especially secretion containing sputum, mucus, saliva as well as blood, which are present there. Such accumulations of secretions increase the flow resistance in the endotracheal tube and thus lead to an elevation of pressure. In addition, an accumulation of secretion triggers an irritation of the throat or cough reflex in the patient, which is superimposed to the normal rhythm of inhalation and exhalation and leads to an elevation of the airway pressure.

Signals of sensors are available for the analysis for analyzing the situation and for determining whether an elevation of the pressure that is caused by the patient is present as a cause for an alarm indicating an elevated airway pressure. These sensors are, for example, pressure sensors and flow sensors, which are located in or at the medical device or are arranged on this or on gas-carrying components or connection systems, for example, tube systems.

Measuring sites of the medical device, at which pressure measurements and flow measurements can be carried out and from which it is possible to determine both the airway pressure and the patient's flow rate, are an inspiratory measuring site and an expiratory measuring site within or at the medical device for the mechanical ventilation of a patient, as well as a measuring site (Y-piece) located close to the patient, outside and proximal to the medical device, for example, in or at the gas-carrying components or connection systems. Three suitable measuring sites for pressure measurement and flow measurement, which are different, in principle, from one another, an inspiratory measuring site and an expiratory measuring site inside the medical device for ventilating a patient, as well as a measuring site (Y-piece) located close to the patient, outside and proximally to the medical device for ventilating a patient are mentioned in Table 1 below.

The measured values that can be obtained at these measuring sites as well as the measured variables that can be derived, calculated or determined from these are shown.

TABLE 1

| Measuring site | Detected measured pressure value | Determinable pressure measured variable | Detected measured flow value | Determinable measured flow variable |
|---|---|---|---|---|
| Inspiratory (inhalation) | Inspiratory pressure $P_{insp}$ | $P_{aw} = P_{insp} - P_{hose\_insp}$ | Inspiratory flow rate $\dot{V}_{insp}$ | $\dot{V}_{Pat} = \dot{V}_{exp} - \dot{V}_{insp}$ |
| Expiratory (exhalation) | Expiratory pressure $P_{exp}$ | $P_{aw} = P_{exp} + P_{hose\_exp}$ | Expiratory flow rate $\dot{V}_{exp}$ | |
| Close to the patient (proximal) | Patient pressure $P_{Pat}$ | $P_{aw} = P_{Pat}$ | Patient flow rate $\dot{V}_{Pat}$ | $\dot{V}_{Pat}$ Quantity & direction |

In Table 1 above, $P_{aw}$=airway pressure, $P_{Pat}$=estimated pressure in the lungs of the patient on the basis of the pressure measured close to the patient, $P_{insp}$=inspiratory pressure at the inhalation outlet of the ventilator, $P_{exp}$=expiratory pressure at the exhalation inlet of the ventilator, $P_{hose\_insp}$=pressure gradient at the inspiratory ventilation tube, $P_{hose\_exp}$=pressure gradient at the expiratory ventilation tube, $\dot{V}_{Pat}$=flow rate at the patient, $\dot{V}_{exp}$=expiratory flow rate into the exhalation inlet of the ventilator, $\dot{V}_{insp}$=inspiratory flow rate from the inhalation outlet of the ventilator.

According to a first aspect of the present invention, the object is accomplished by a method according to the present invention for determining an operating situation in a medical device configured as an anesthesia apparatus or ventilator.

The method according to the present invention is configured for detecting operating situations that indicate disturbances in the supply and the removal of breathing gases from the airways of a patient and for providing the output of a control signal indicating this operating situation for alarming on the basis of the detected operating situations.

The anesthesia apparatus or ventilator is configured for processing sensor signals provided by sensors arranged in or at the anesthesia apparatus or ventilator or connected to the anesthesia apparatus or ventilator. The sensor signals indicate pneumatic/fluidic physical states of a breathing gas in a gas-carrying connection system connected to and coupled with the anesthesia apparatus or ventilator and to a patient in a gas-carrying manner, which system is configured for transporting gases from and to the patient. The connection system is preferably configured as a ventilation tube, also preferably as a combination of an inspiratory ventilation tube and an expiratory ventilation tube. As an alternative to this, a coaxial ventilation tube system may be used.

Values of an airway pressure $P_{AW}$ currently present in the gas-carrying connection system and of a flow rate flowing in the gas-carrying connection system as well as of the flow rate in flow directions belonging to the gas-carrying connection system may be determined from the sensor signals.

The method according to the present invention for determining an operating situation uses these sensor signals to determine the airway pressure $P_{AW}$ as well as to determine and classify an operating state in the gas-carrying connection system and/or medical device.

An analysis is carried out in respect to the onset of individual cough events as well as in respect to a clustering of a plurality of individual cough events during a checking time interval, and an operating situation is determined based on this to determine whether an operating situation, which indicates disturbances in the supply and in the removal of breathing gases from the airways of a patient, is present and the output of a control signal indicating this operating situation is provided for generating an alarm.

This classification of the operating state of the medical device by the method according to the present invention makes it possible to determine whether, due to a plurality of individual temporary elevations of the airway pressure $R_{AW}$, which one initial cough event occurring during an expiratory phase (exhalation) is followed in time, an operating situation of the medical device is present, for which a certain number of individual cough events, such as a sequence of individual coughing fits, is characteristic as a cough sequence during the checking time period for a cough sequence and it can then be classified as an operating situation that indicates an accumulation of secretion.

Temporary elevations of the airway pressure $P_{AW}$ during the expiratory phases (exhalation) are assessed as initial cough events.

An initial cough event, which develops during an expiratory phase (exhalation) and can be detected in the medical device by measurement by means of the temporary elevation of the airway pressure $P_{AW}$, is assessed as a possible beginning of a subsequent cough sequence. This initial cough event is therefore detected with the time of onset of the event (time stamp) and stored in a memory.

Additional temporary elevations of the airway pressure $P_{AW}$ are subsequently assessed during the same expiratory phase (exhalation) as well as during the subsequent phase of an inhalation as a sequence of cough events (cough sequence). If a predefined number of cough events (cough sequence), i.e., of elevations of the airway pressure $P_{AW}$ above a predefined threshold value selected as a comparison criterion occur during a checking time interval, which begins with the initial cough event and lasts for a predefined time, this is assessed such that the medical device is being operated in an operating situation in which an accumulation of secretion is indicated. This accumulation of secretion may be present both in regions of the lungs, regions of the bronchi, regions of the trachea as well as in the endotracheal tube itself. This operating situation, which indicates an accumulation of secretion, causes the medical device to provide or output a control signal or an output, which is characteristic of this operating situation.

The signal may be, for example, a signal that makes it possible to output a warning, a message, an acoustic alarm or a visual alarm to the medical staff directly at the medical device. Such a control signal may, however, also be transmitted to a remote unit for outputting alarms and messages, for example, in a monitoring room, or to a mobile data output system (pager, mobile phone) by means of suitable and usual data transmission channels (telephone, SMS, LAN, WLAN, network, Bluetooth).

The following steps are carried out in a recurring sequence of steps in the method for determining an operating situation in a medical device:

detection of pneumatic-fluidic states in the gas-carrying connection system with determination of values of pressure and flow rates, comparison on the basis of the values determined for the airway pressure PAW whether a comparison criterion indicating the airway pressure PAW is exceeded by the currently determined value of the airway pressure PAW, determination of whether the medical device is in an operating state in which a smaller quantity of breathing gas is being fed to the patient by the medical device than flows away from the patient on the basis of a comparison of whether a comparison criterion indicating a flow rate and a flow direction is given by the value determined for the flow rate and by the determined flow direction, checking whether at least one cough event or a plurality of cough events has/have occurred during a checking time interval since a chronologically preceding checking time, initialization of the checking time interval and start of a detection of a number of cough events, if at least one cough event has occurred during the checking time interval since the chronologically preceding checking time, and if the medical device is currently in the operating state in which a smaller quantity of breathing gas is fed by the medical device to the patient than flows away from the patient, and if the comparison criterion indicating the airway pressure PAW is exceeded by the currently determined value of the airway pressure PAW, continuation of the detection, counting and recording of the number of cough events, if at least one cough event has occurred during the checking time interval since the chronologically preceding checking time, and if the comparison criterion indicating the airway pressure PAW is exceeded by the currently determined value of the airway pressure PAW, comparison of the number of cough events detected during the checking time interval with a predefined comparison number, determination, on the basis of the comparison concerning the detected number of cough events in relation to the predefined comparison number, whether an operating situation, which indicates an accumulation of secretion, is present, and provision of a control signal, which indicates the operating situation in which secretion accumulates.

The operating state in which a larger quantity of breathing gas is fed or flows by way of the medical device by means of an inspiratory connection system (inspiratory ventilation tube) to the patient than flows away from the patient corresponds here to the inspiratory phase (inhalation).

The operating state in which a smaller quantity of breathing gas is fed or flows to the patient by way of the medical device than flows away from the patient and flows, for example, back into the medical device via an expiratory connection system, now corresponds to the expiratory phase (exhalation). There are situations in both inspiratory phases (inhalation) and in expiratory phases (exhalation) in which additional quantities of exhaled breathing gas are present as at least temporary elevations of the flow rate in the gas-carrying connection system (ventilation tube) and lead to elevations of the airway pressure $P_{AW}$ due to a cough event or a plurality of cough events or cough sequences.

These at least temporary elevations of the airway pressure $P_{AW}$ as an indicator of the operating state with disturbances in the supply and in the removal of breathing gases from the airways of a patient are determined on the basis of the sensor signals of the sensors (pressure, flow rates) arranged at the measuring sites of the medical device or at the gas-carrying connection system.

A minimum number of more than five cough events, which can usually be observed during a time interval of five to fifteen minutes in a patient with an accumulation of secretion in the airways in routine clinical practice, may preferably be selected as a predefined comparison number as an indicator of the operating situation in which secretion accumulates.

Signals of at least one pressure sensor, whose signals indicate the at least temporary elevations of the airway pressure $P_{AW}$, are preferably used as the basis for the values for determining the airway pressure $P_{AW}$ in the method for determining the operating situation.

This at least one pressure sensor is preferably arranged at the connection system close to the mouth/nose area of the patient at the patient connection path or at the connection element (Y-piece).

The at least one pressure sensor or another pressure sensor is also preferably arranged at the inspiratory connection system.

The at least one pressure sensor or another pressure sensor is also preferably arranged at the expiratory connection system.

A predefined pressure threshold value is preferably selected in another embodiment as a possible comparison criterion, which indicates an elevated airway pressure $P_{AW}$. Thus, a pressure value above a pressure threshold value, for example, 30 hPa±3 hPa, characterizes, for example, an elevated airway pressure for an adult patient.

Thus, a pressure value above a pressure threshold value of 20 hPa±2 hPa characterizes, for example, an elevated airway pressure for a pediatric patient.

To determine whether the medical device is in an operating state in which a smaller quantity of breathing gas is fed by the medical device to the patient than flows away from the patient, it is determined in a preferred embodiment of the method on the basis of a comparison whether a comparison criterion indicating a flow rate and a flow direction is exceeded by the determined value of the flow rate and by the determined flow direction.

A possible comparison criterion, which indicates the flow rate and the flow direction, is a predefined flow rate threshold value associated with a flow direction. Thus, a flow rate above a flow threshold value of, e.g., about 2.5 L/min±0.2 L/min characterizes, for example, with a corresponding flow direction away from the patient, an exhalation.

Thus, a flow rate above a flow rate threshold value of, e.g., 1.5 L/min±0.2 L/min characterizes, for example, with an associated flow direction towards the patient, an inhalation. For example, a flow rate below a flow rate threshold value of, e.g., 2.5 L/min±0.2 L/min thus characterizes, with an associated flow direction away from the patient, the end of an exhalation or an expiratory pause. For example, a flow rate below a flow rate threshold value of, e.g., 1 L/min±0.2 L/min thus characterizes, with an associated flow direction towards the patient, the beginning or the end of an inhalation or an inspiratory pause. These flow rates are determined on the basis of the sensor signals of the sensors arranged at the measuring sites of the medical device or at the gas-carrying connection system.

Signals of at least one flow sensor, whose signals indicate the flow rates and flow directions in the connection system, are preferably used for this in the method for determining the operating situation.

This at least one flow sensor is preferably arranged at the connection system close to the mouth/nose area of the patient at the patient connection path or at the connection element (Y-piece).

The at least one flow sensor or another flow sensor is also preferably arranged at the inspiratory connection system.

The at least one flow sensor or another flow sensor is also preferably arranged at the expiratory connection system.

To determine whether the medical device is in an operating state in which a smaller quantity of breathing gas is fed by the medical device to the patient than flows away from the patient, at least information from a course of the control of the medical device concerning the current phase of breathing or information concerning a state of an expiratory valve or an actuating signal for such an expiratory valve is taken into account in another preferred embodiment of the method. It is possible with this information on the state of the valve (closed, opened, degree of setting) to verify, especially during ventilation with mandatory ventilation modes, from the course of the control whether a smaller quantity of breathing gas is fed by the medical device to the patient than flows away from the patient, i.e., whether an expiratory phase (exhalation), usually preset mandatorily by the medical device, is present as far as the medical device is concerned.

The medical device brings about, by means of the control during the mechanical, for example, mandatory or assisted ventilation, the continuous course of expiratory phases (exhalation) and inspiratory phases (inhalation) on the basis of the respiration rate (RR) and of the inspiration time to expiration time ratio (I:E ratio).

In a preferred embodiment of the method, the checking time interval begins with the initial cough event and ends after a predefined duration in a time range of 5 minutes to 15 minutes after the initial cough event.

The duration of a breathing cycle is 3 sec to 6 sec in an adult at rest or during light physical exercise. This corresponds to a respiration rate of 10 to 20 breathing cycles per minute, i.e., inspiratory phases (inhalation) and corresponding expiratory phases (exhalation), in an adult or adolescent. By contrast, the respiration rate of a newborn, equaling 40 to 50 breathing cycles per minute, is markedly higher.

A number of 30 to 300 consecutive breathing cycles, i.e., 30 to 300 inspiratory phases (inhalation) and correspondingly with 30 to 300 expiratory phases (exhalation) is selected for the checking time interval in a preferred embodiment of the method.

Five to fifteen cough events, which indicate that the operating situation with accumulation of secretion is present, usually occur during such a checking time interval.

A number of at least two cough events occurring at a predefined time interval during an expiratory phase (exhalation) is determined as an initial cough event in a preferred embodiment of the method. A time interval of 0.3 sec to 5 sec may preferably be selected as a predefined time interval.

In a preferred embodiment of the method, the number of cough events is counted, beginning from the initial cough event, decrementing towards the value of zero beginning from the predefined comparison number.

In another, likewise preferred embodiment of the method, the number of cough events is counted, beginning from the initial cough event, from a start value, which is preferably a value of zero, incrementing up to the predefined comparison value.

These methods of counting cough events are, in effect, equivalent for the determination of the operating situation, which indicates an accumulation of secretion. Of the two methods, the method that is implemented in practice in the process is the one that is more advantageous for the implementation concerning the process control and memory requirement.

The embodiments described represent special embodiments of the method according to the present invention for determining operating situations in an anesthesia apparatus or ventilator in themselves as well as in combination or combinations with one another. All and possible additional embodiments arising through a combination or combinations of a plurality of embodiments and their advantages are likewise covered by the inventive idea, even though not all possibilities of combining embodiments are specifically described for this in detail. The above-described embodiments of the method according to the present invention may also be configured in the form of a computer-implemented method as a computer program product with a computer, wherein the computer is prompted to execute the method according to the present invention when the computer program is executed on the computer or on a processor of the computer or on a so-called "embedded system" as part of a medical device. The computer program may also be stored on a machine-readable storage medium. In an alternative embodiment, a storage medium, which is intended for storing the above-described, computer-implemented method and can be read by a computer, may be provided. It is within the scope of the present invention that not all steps of the method have necessarily to be executed on one and the same computer, but they may also be executed on different computers. The sequence of the method steps may possibly also be varied. It is furthermore possible that individual sections of the above-described method are executed in a separate unit, which can be sold, for example, by itself.

The solution for accomplishing the object was described above with respect to the method claimed as a first aspect of the present invention. In addition, a medical device according to the present invention, which is configured to carry out the method according to the present invention in the sense of at least one of the embodiments described, arises as another aspect. Features mentioned for the method, described advantages or alternative embodiments can likewise be applied to the other claimed subjects as well and vice versa. The corresponding functional features of the method are configured here by corresponding physical modules of a device, especially by hardware components (μC, μP, DSP, FPGA, ASIC, GAL, logical units), which may be implemented, for example, in the form of a processor (μP), a plurality of processors or in the form of instructions in an internal or external memory or memory area, which are processed by the processor.

The advantages described for the method according to the present invention can be achieved in the same manner or in a similar manner with the device according to the present invention. Furthermore, the described embodiments and their features and advantages of the method can be applied to the device, and the described embodiments of the device can just as well be applied to the method.

The object of determining an operating situation is also accomplished according to the present invention by a medical device according to the additional aspect of the present invention.

This medical device, embodied as an anesthesia apparatus or ventilator, is configured for the mechanical, mandatory or assisted ventilation of a patient and has for this, according to the present invention, a connection system configured for transporting breathing gases, a pressure-measuring unit, a flow-measuring unit, a control unit, a dispensing unit and an alarm generation unit. The control unit is preferably configured as a microprocessor module (μC) with associated internal and/or external memory (RAM). The flow-measuring unit as well as the pressure-measuring unit are configured for converting electrical signals, which indicate physical measured variables and which are provided by the flow sensors and pressure sensors, into data signals suitable for data processing. In usual configurations of anesthesia apparatuses and ventilators, the flow-measuring unit, the pressure-measuring unit and the alarm generation unit are configured as components or modules of the control unit.

The connection system has an expiratory path, which is configured and intended for removing an expiratory quantity of breathing gas from the patient. The connection system has an inspiratory path, which is configured and intended for feeding an inspiratory quantity of breathing gas from the medical device to the patient. The connection system has a patient connection path, which is configured and intended for feeding the inspiratory quantity of breathing gas from the medical device to the patient and for removing the expiratory quantity of breathing gas from the patient. The expiratory path and the inspiratory path are connected to one another and to the patient connection path by means of a connection component. The connection component may be and is often configured in practice as a so-called Y-piece.

The flow-measuring unit has at least one flow sensor, which is arranged on the connection system or in or at the medical device and is intended for detecting at least one flow rate of a quantity of breathing gas that is flowing away from the patient in the connection system or is flowing from the medical device to the patient. The flow-measuring unit is configured to provide this at least one flow rate measured value to the control unit.

The pressure-measuring unit has at least one pressure sensor, which is arranged in or at the medical device or at the connection system and is intended for detecting a measured value of a pressure, which is present in the connection system, and the pressure-measuring unit is configured to provide this at least one pressure measured value to the control unit.

The control unit is configured in a suitable manner, preferably by means of an interface, to receive pressure measured values and flow measured values, preferably from the pressure-measuring unit and from the flow-measuring unit, or to input them via a data connection.

The control unit is configured in a suitable manner for comparing the detected pressure measured value with a predefined pressure threshold value and to determine on the basis of the comparison whether the detected pressure measured value indicates a temporary elevation of the airway pressure $P_{AW}$. This at least temporary elevation of the pressure as an indicator of the operating state of the exhalation and/or cough event or coughing fit is determined on the basis of the sensor signals of the pressure and flow sensors.

The control unit is configured in a suitable manner in conjunction with the dispensing unit to control or regulate an array of valves in order to allow a course of a ventilation with pressure control or volume control, limit value monitoring for pressures and volumes with the selection of a respiration rate and durations (I:E) of the inspiratory phase (inhalation) and expiratory phases (exhalation) to take effect by means of the medical device at the patient.

The control unit is further configured to compare the at least one detected flow rate measured value with a predefined flow rate threshold value and to determine on the basis of the comparison whether the at least one flow rate measured value exceeds a predefined flow rate threshold value.

The control unit is further configured to determine whether the at least one flow rate measured value and the corresponding flow direction indicate an operating state of a phase of an exhalation with a flow rate and with a flow direction belonging to the flow rate in which phase the quantity of breathing gas flowing towards the patient is smaller than the quantity of breathing gas flowing away from the patient.

The pressure and flow threshold values are preferably provided directly to the control unit or, as an alternative, they are provided indirectly with involvement of the memory.

An alternative as well as additional possibility of determining the operating state in which a smaller quantity of breathing gas is fed by the medical device by means of the inspiratory path of the connection system or flows towards the patient than the quantity flowing away from the patient by means of the expiratory path of the connection system arises for the control unit from the utilization of information from the course of the ventilation with a control of inspiratory phases (inhalation), expiratory phases (exhalation), volumes (Vt) and ventilation pressures ($P_{insp}$, $P_{exp}$, PEEP).

The control unit is thus configured to determine that an operating state is present in which a smaller quantity of breathing gas is fed from the medical device by means of the inspiratory path of the connection system or flows to the patient than flows away from the patient by means of the expiratory path of the connection system. This operating state corresponds to an operating state of an exhalation, i.e., to a phase of the exhalation.

This operating state of the exhalation represents a situation in which there is, due to a cough event or a coughing fit, an additional quantity of exhaled breathing gas as an at least temporary increase in the flow rate in the gas-carrying connection system and the predefined pressure threshold value was caused to be exceeded by the pressure measured value due to the cough event or coughing fit.

The control unit is therefore further prepared and configured to determine as an initial cough event the state when the at least one flow rate measured value exceeds the predefined flow rate threshold value and the detected pressure measured value exceeds the predefined pressure threshold value and the operating state of the expiratory phase (exhalation) is present.

The control unit is further prepared and configured to determine additional cough events continuously in the further process and course of the operation of the medical device in case the at least one flow rate measured value exceeds the predefined flow rate threshold value and the detected pressure measured value exceeds the predefined pressure threshold value. Both the operating state of the expiratory phase (exhalation) or an operating state of a phase of the inhalation may be present now. A sequence of operating states with a plurality of inhalations and exhalations may be present as well.

Furthermore, the control unit is configured to determine the number or frequency of cough events beginning from the initial cough event determined during a phase of the exhalation in a checking time interval.

The control unit is further configured to compare the number or the frequency of cough events during the checking time interval with a predefined comparison number, which is provided for the control unit preferably from the memory, and to determine on the basis of this comparison an operating situation that indicates an accumulation of secretion. This accumulation of secretion may occur both in regions of the lungs, regions of the bronchi, regions of the trachea as well as in the endotracheal tube itself.

Furthermore, the control unit is configured to provide a control signal at an interface, for example, for transmission into a data network (LAN, WLAN), which indicates the operating situation of an accumulation of secretion.

The control unit is further configured for activating and/or deactivating the alarm generation unit for outputting an alarm of a visual and/or acoustic warning indicating the operating situation of the accumulation of secretion.

The medical device determines an operating situation of an accumulation of secretion by means of the control unit, said control unit being configured to determine or input at least one pressure measured value, to determine a current airway pressure PAW on the basis of the at least one pressure measured value, to make a comparison based on the determined values of the airway pressure PAW whether the current, determined value of the airway pressure PAW exceeds a comparison criterion indicating the airway pressure PAW, to determine or input at least one flow measured value, to determine whether the medical device is in an operating state in which a smaller quantity of breathing gas is fed by the medical device to the patient than flows away from the patient, on the basis of information from the course of the ventilation, and/or information concerning a state of an expiratory valve or an actuating signal for such an expiratory valve, and/or on the basis of a comparison of whether a comparison criterion indicating a flow rate and a flow direction is exceeded by the determined value of the flow rate and by the determined flow direction, to check whether a cough event or a plurality of cough events has/have occurred during a checking time interval since a chronologically preceding checking time, to initialize (restart) the checking time interval and to begin the detection of a number of cough events, if at least one cough event has occurred during the checking time interval since the chronologically preceding checking time, and if the medical device is currently in the operating state in which a smaller quantity of breathing gas is fed by the medical device to the patient than flows away from the patient, and the comparison criterion indicating the airway pressure PAW is exceeded by the currently determined value of the airway pressure PAW, to continue the detection, counting and recording of the number of cough events, if at least one cough event has occurred during the checking time interval since the chronologically preceding checking time, and if the medical device is currently in the operating state in which a smaller quantity of breathing gas is fed by the medical device to the patient than flows away from the patient, and if the comparison criterion indicating the airway pressure PAW is exceeded by the currently determined value of the airway pressure PAW, to compare the number of cough events detected during the checking time interval with a predefined comparison number, to determine on the basis of the comparison concerning the detected number of cough events in reference to the predefined comparison number whether the operating situation that indicates an accumulation of secretion is present, and to provide a control signal, which indicates the operating situation with an accumulation of secretion.

The control unit is enabled by means of the information on the state of the expiratory valve (closed, opened, degree of setting), especially during operation with control of a mandatory ventilation, to directly identify from the course of the process mandatory expiratory phases (exhalation) as states in which smaller quantities of breathing gas are fed by the medical device to the patient than flow away from the patient.

A number of at least five or more cough events, which can usually be observed in the checking time interval of five to fifteen minutes in a patient with an accumulation of secretion in the airways in routine clinical practice, can preferably be selected by the control unit as a predefined comparison number as an indicator of the operating situation with accumulation of secretion.

In a preferred embodiment of the medical device, at least one pressure sensor, which is configured for signal transmission of a value that indicates the airway pressure $P_{AW}$ to the control unit, is arranged and configured for detecting the pressure at the connection element (Y-piece).

In a preferred embodiment of the medical device, at least one pressure sensor or another pressure sensor, which is configured for a signal transmission of a value that indicates the airway pressure $P_{AW}$ to the control unit, is arranged and configured for detecting the pressure at the inspiratory connection system (ventilation tube).

In a preferred embodiment of the medical device, at least one pressure sensor or another pressure sensor, which is configured for signal transmission of a value that indicates the airway pressure $P_{AW}$ to the control unit, is arranged at the expiratory connection system (ventilation tube) for detecting the pressure.

In a preferred embodiment of the medical device, at least one flow sensor, which is configured for signal transmission for transmitting a signal that indicates flow rates from or to the patient to the control unit, is arranged at the patient connection path or at the connection element (Y-piece) for detecting the flow rate and flow directions.

The control unit is configured to determine whether the medical device is in an operating state in which a smaller quantity of breathing gas is fed to the patient than flows away from the patient on the basis of the signal of the flow sensor at the patient connection path or at the connection element (Y-piece).

In a preferred embodiment of the medical device, at least one flow sensor or another flow sensor for detecting an inspiratory flow rate, which is configured for the signal transmission of a signal that indicates an inspiratory flow rate to the control unit, is arranged at the inspiratory connection system (ventilation tube).

In a preferred embodiment of the medical device, at least one flow sensor or another flow sensor for detecting an expiratory flow rate, which is configured for the signal transmission of a signal that indicates an expiratory flow rate to the control unit, is arranged at the expiratory connection system (ventilation tube).

In another preferred embodiment, the control unit is configured to determine whether the medical device is in an operating state in which a smaller quantity of breathing gas is fed by the medical device to the patient than flows away from the patient on the basis of a difference from the signals of the flow sensor arranged in or at the expiratory path of the connection and of the flow sensor arranged in or at the inspiratory path of the connection system.

The control signal is provided in a preferred embodiment by the control unit to an output unit or to the alarm generation unit.

The output unit is configured to transmit the control signal, which indicates an operating situation with accumulation of secretion, directly or by means of an interface (WLAN, LAN, RS232, data bus, IrDA) into a network (intranet, internet, PAN, WAN) and/or to an analysis unit (monitoring station, patient data management system).

In a preferred embodiment, the alarm generation unit is configured to output an alarm for a visual and/or acoustic warning or alarm indicating the operating situation with accumulation of secretion. Acoustic alarms may be outputted now, for example, by means of a sound-emitting component (loudspeaker, horn, speech output).

Visual alarms may be outputted or displayed, for example, by means of a display screen (screen, touchscreen, tablet PC, smartphone), an illuminant (LED, LED), and also in text form (LCD row, LED row, dot matrix display).

In a preferred embodiment, a predefined pressure threshold value is selected by the control unit as a comparison criterion for the airway pressure $P_{AW}$.

Thus, a pressure value above a pressure threshold value of 30 hPa±3 hPa characterizes, for example, an elevated airway pressure for an adult patient.

Thus, a pressure value above a pressure threshold value of 20 hPa±2 hPa characterizes, for example, an excessive airway pressure for a pediatric patient.

In a preferred embodiment, the checking time interval is selected by the control unit such that the checking time interval begins with the initial cough event and ends after a predefined duration in a time range of 5 minutes to 15 minutes after the initial cough event.

In a preferred embodiment, the checking time interval is selected by the control unit for the checking time interval to be a number of 30 to 300 consecutive breathing cycles.

In a preferred embodiment, the control unit selects as the initial cough event a number of at least two cough events occurring during a predefined time period, preferably during a time period of 0.3 sec to 5 sec, in the operating state in which a smaller quantity of breathing gas is fed by the medical device to the patient than flows away from the patient.

In a preferred embodiment, the counting of the number of cough events is carried out by the control unit beginning with the initial cough event and incrementing to the predefined comparison number.

As an alternative, the counting of the number of cough event is carried out by the control unit beginning with the predefined comparison number decrementing towards a value of zero.

These two methods of counting the number of cough events are, in effect, equivalent for the determination of the operating situation that indicates an accumulation of secretion. Of the two methods, the method that is carried out in the control unit is the one that its more advantageous for the implementation for the determination of the operating situation concerning the memory requirement and process control.

The present invention will be explained in more detail now by means of the following figures and the corresponding description of the figures without limitation of the general inventive idea. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
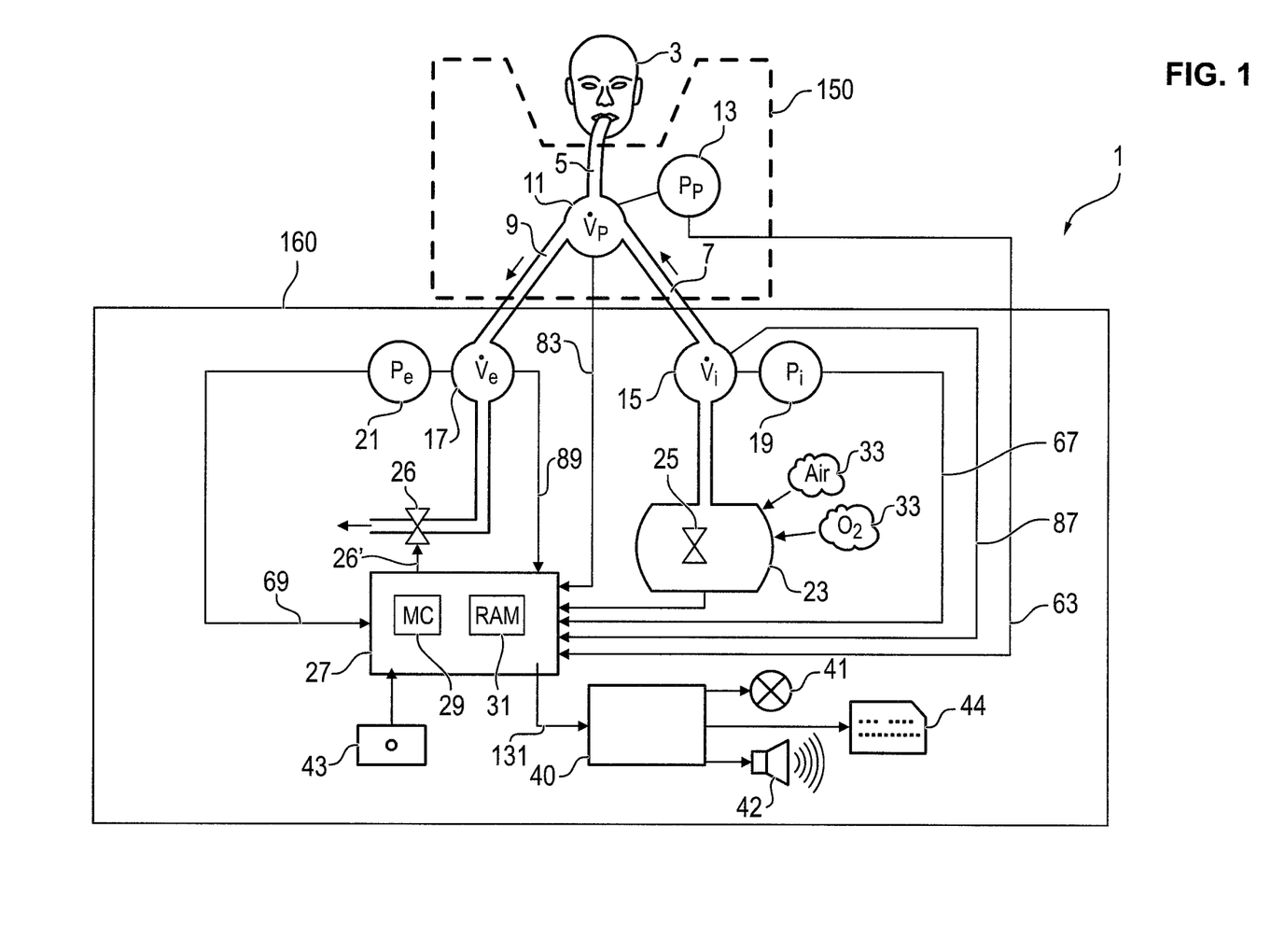
FIG. 1 is a schematic view of a medical device configured suitably for a mechanical ventilation.

Referring to the drawings, FIG. 1 shows a schematic view of a medical device or system of medical devices configured suitably for mechanical ventilation, for example and preferably a ventilator 1 with its essential components. The ventilator 1 has a control unit 27, which is preferably configured as an electronic control unit, which is configured suitably and intended for controlling or regulating a gas-mixing and -dispensing unit 23 with a dispensing valve device 25 arranged therein. Furthermore, measuring sites 15, 17, 19, 21 inside the ventilator 1 are shown in the ventilator 1. A measuring site for the inspiratory flow rate 15 and a measuring site for an inspiratory pressure 19 are arranged downstream of the gas-mixing and -dispensing unit 23. An inspiratory branch 7 of a patient gas supply line 5, via which the ventilator 1 supplies breathing gas to the patient 3 for inhalation, is arranged following said measuring sites 15, 19. A measuring site for the patient flow rate 11 and for a patient pressure 13, starting from which the patient 3 is connected to the ventilator 1 via a patient gas supply line 5 usually configured as an endotracheal tube for exchanging inhaled and exhaled air, are connected to a so-called Y-piece directly at the patient 3, outside 150 the ventilator 1, but cooperating with the ventilator 1.

As an alternative to the endotracheal tube, it is also possible to use non-invasive components for the patient gas supply as a patient gas supply line 5, such as masks, for example, nasal masks at the Y-piece. The air exhaled by the patient 3 is returned during exhalation to the ventilator 1 from the Y-piece at the patient 3 via an expiratory branch 9 of the patient gas supply line 5.

To control the ventilator 1 for the purpose of ventilation control (breathing cycle, respiration rate, expiratory ventilation pressure), the pressure in the expiratory branch 9 and hence also the pressure present in the lungs of the patient 3 are set by means of an actuating signal 26' by the control unit 27 by means of an expiratory valve 26, often also called "PEEP" valve.

In addition, the control of the ventilation with cyclical alternation of inspiratory phases (inhalation) and expiratory phases (exhalation) (breathing cycle, respiration rate) is brought about via the expiratory valve 26 in conjunction with the control unit 27 and with the gas-mixing and -dispensing unit 23 with the dispensing valve device 25 arranged therein. A measuring site for the expiratory flow rate 17 and a measuring site for an expiratory pressure 21 are arranged inside or in the interior 160 of the ventilator 1 downstream of the expiratory branch of the patient gas supply line 9. In alternative and special embodiments of ventilators 1, which are specially adapted to the application, such as emergency respirators or home ventilators as well as in anesthesia apparatuses that also have components for ventilation in addition to the components necessary for an anesthesia, measuring sites and components (sensors) may be distributed in relation to the components in the interior 160 and outside 150 differently from the embodiment shown in a simplified manner in this FIG. 1. For example, the components 15, 17, 19, 21 may thus be arranged outside 150 as well as also inside 160 the ventilator.

Such embodiments are also covered by the inventive idea, but they are not shown for reasons of a simplified view and for reasons of clarity. The exhaled air of the patient 3 is removed from these measuring sites 17, 21 to the surrounding area. The measuring sites 11, 13, 15, 17, 19, 21 and the flow sensors and pressure sensors, which are arranged at these measuring sites but are not shown in detail in this FIG. 1 for reasons of clarity, are connected each to the control unit 27 via respective suitable signal and data lines 63, 67, 69, 83, 87, 89. A flow-measuring unit and a pressure-measuring unit, which are not shown in this FIG. 1 for reasons of clarity, are configured in this FIG. 1 as units integrated into the control unit 27. In addition to the flow-measuring unit and the pressure-measuring unit, the control unit 27 has suitably configured data processing and conversion units (signal amplification, signal filtering, A/D conversion), which are not shown in this schematic view according to FIG. 1, as well as a processor unit 29 and a memory unit 31 in order to configure and carry out the process of ventilation by and with the ventilator 1. Gases 33 needed for the ventilation, such as oxygen and air, are supplied to the gas-mixing and -dispensing unit 23 by means of supply lines not shown in FIG. 1 and converted there by the dispensing valve device 25 into a gas mixture, which is suitable for ventilating the patient 3.

Figure 2:
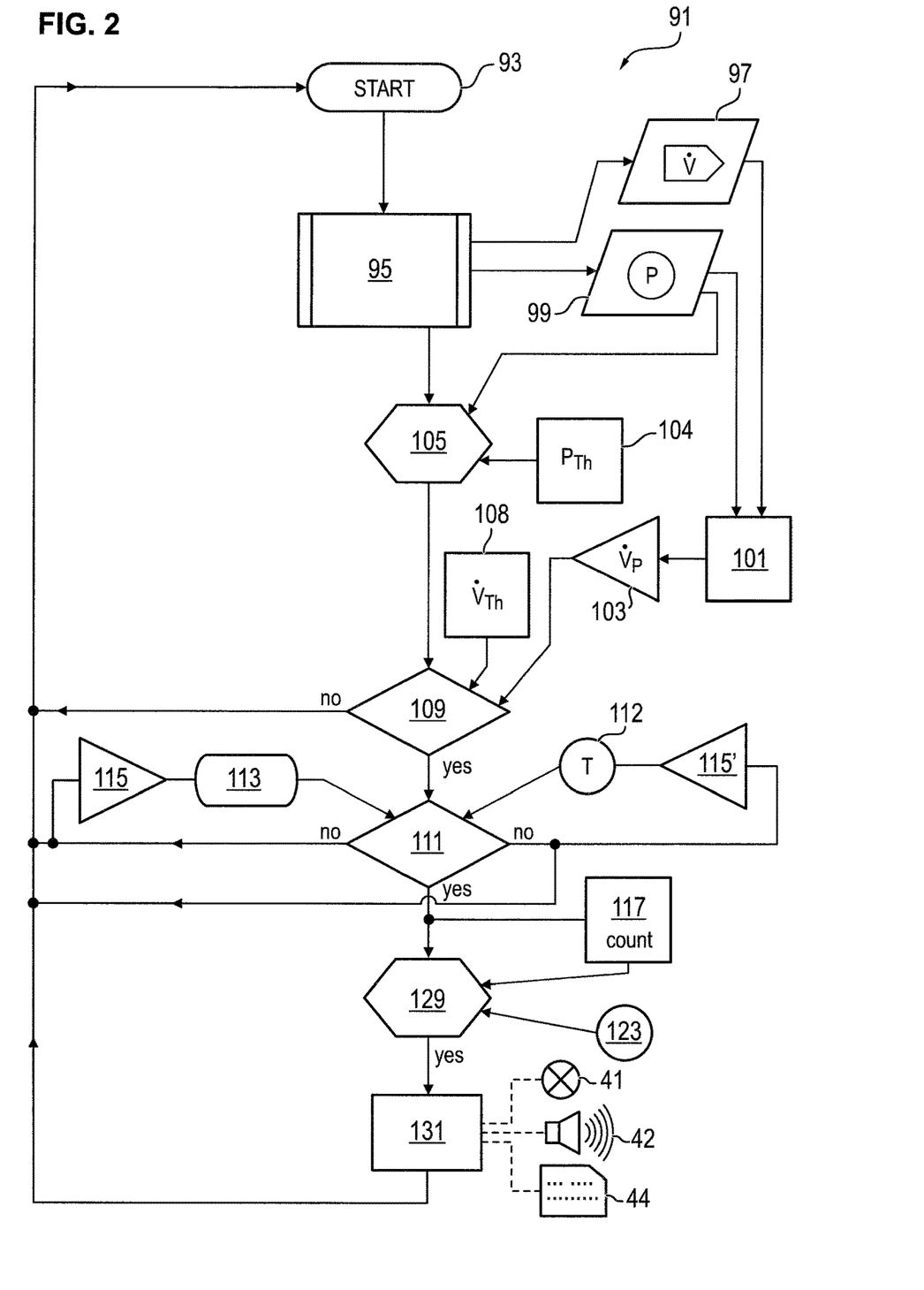
FIG. 2 is a flow diagram showing a sequence of functions and steps for the determination of an operating situation that indicates an accumulation of secretion.

An alarm generation unit 40 with an optical signal generation unit 41 and with an acoustic signal generation unit 42 is connected to the control unit 27 in a wireless or wired manner in order to signal alarm situations that may occur during the operation of the ventilator 1 to the user. The connection is brought about such that a control signal 131 is provided by the control unit 27. The control signal 131 indicates whether an operating situation with an accumulation of secretion has occurred or is occurring during the checking time interval 112 (FIG. 2). Furthermore, an output unit 44 for an output in text form or in graphic form is arranged at the alarm generation unit 40 in order to output notices, alarms and messages to the user, for example, a warning concerning an operating situation with possible accumulations of secretion. In addition, an input unit 43, via which the user can perform both settings, such as operating parameters, e.g., respiration rate, tidal volume, ventilation pressures ($P_{insp}$, PEEP) and corresponding alarm limits, such as a maximum allowable airway pressure ($P_{aw-high}$), volume limits (MVLow) on the ventilator 1 and can also acknowledge signaled alarm situations, is connected to the control unit 27.

FIG. 2 shows in a schematic view of a sequence of functions and steps a process for determining an operating situation which indicates an accumulation of secretion in a ventilator or in an anesthesia apparatus. A sequence of steps and functions 91 with a start 93, with an overall function of a ventilation operation 95, as well as additional steps and functions taking place in the process and in cooperation with measured values of the flow 97 and pressure 99 during the ventilation operation 95 are shown. Pressure measured values 99 and/or flow measured values 97, which are merged in a measured value analysis unit 101 and are subsequently sent to a patient flow analysis 103, occur during the regular operation 95, which is shown here schematically as a function block. The flow measured values 97 from the ventilation operation as well as the pressure measured values 99 from the ventilation operation are provided by the ventilator 1 (FIG. 1) for the control unit 27 (FIG. 1) through signals and data lines 63, 67, 69, 83, 87, 89 (FIG. 1). This control unit 27 (FIG. 1) controls the ventilation operation 95 according to this FIG. 2 during the entire operation 95 as well as the procedure of determining an operating situation with an accumulation of secretion, as it further appears from FIG. 2.

The patient flow analysis 103 is performed in order to determine whether there is at the moment and currently a patient flow from the patient 3 (FIG. 1) to the ventilator 1 (FIG. 1) in order to determine the particular current inspiratory phase (inhalation) and exhalation in the patient 3 (FIG. 1) and/or at the ventilator 1 (FIG. 1). In addition to the pressure measured values 99 and/or flow measured values 97, information from the control of the ventilation, for example, from the control unit 27 (FIG. 1) concerning the current phase of breathing, respiration rate as well as the inspiration time to expiration time ratio, may be taken into account in the patient flow analysis 103.

A situation with an at least temporary elevation of the airway pressure ($P_{AW}$) 105 is obtained according to FIG. 2 from the regular and routine ventilation operation 95. This elevation of the airway pressure 105 ($P_{AW}$) indicates that a predefined pressure threshold value 104 is exceeded by the pressure measured values 99.

It is checked in a case distinction 109 whether this temporary elevation of the airway pressure 105 is due to the flow rate caused by the patient. Exceeding the flow threshold value 108 in conjunction with a flow direction with a flow rate flowing away from the patient indicates that the cough event or coughing fit was the cause of the at least temporary elevation of the airway pressure 105 ($P_{AW}$). Information from the control unit (27) (FIG. 1) that the ventilator 1 (FIG. 1) is currently being operated in an expiratory phase (exhalation), based on a mandatory initiation of the expiratory phase (exhalation) or based on an initiation of the expiratory phase (exhalation) caused by the patient by means of a pressure and/or flow trigger, likewise indicates in itself, as well as in conjunction with the flow rate flowing away from the patient, that the at least temporary elevation of the airway pressure 105 ($P_{AW}$) will have been caused by a cough event or coughing fit. If the at least temporary elevation of the airway pressure 105 ($P_{AW}$) was not caused by at least one cough event, the sequence of steps and functions jumps back to the start 93.

If the temporary elevation of the airway pressure 105 was caused by the patient, it is subsequently checked in another case distinction 111 whether a cough event or a plurality of cough events had already occurred within a checking time interval 112 already before this temporary elevation of the airway pressure 105 since a chronologically preceding checking time and if it was recorded as an initial cough event 113.

A duration of 5 minutes to 15 minutes is selected as the checking time interval 112 for the determination of operating states that indicate accumulations of secretion in the lungs or the airways of a patient. The checking time interval thus typically covers a number of 30 to 300 breathing cycles with a respective inspiratory phase (inhalation) and a respective expiratory phase (exhalation) each with a breathing cycle duration of about 3 to 6 sec. Five to fifteen cough events usually occur during such a checking time interval 112.

If the case distinction 111 yields the result that there has not been at least one cough event since the chronologically preceding checking time, this temporary elevation of the airway pressure 105 is assessed to be an initial cough event 113 and the initial cough event 113 is recorded by means of a mark 115 (SET) and the checking time interval 112 is started by means of an additional mark 115' (RESET), for example, with a resetting of a time measurement. The process subsequently jumps back to the start 93 of the sequence of steps and functions 91 and the process is continued and performed with the checking time interval for determining the operating situation that indicates an accumulation of secretion.

If the case distinction 111 yields the result that one cough event or a plurality of cough events have occurred since the chronologically preceding checking time, this temporary elevation of the airway pressure 105 is assessed to be an additional cough event 117 and is counted as an additional cough event 117 following the initial cough event 113.

It is subsequently checked in another case distinction 129 whether a number of cough events, which number exceeds a predefined value 123, have occurred within the checking time interval. If the number of counted cough events 117 in the checking time interval 112 has exceeded the predefined value 123, a control signal 131 is provided, which indicates the operating situation with an accumulation of secretion and continues the sequence of functions 91, the process jumps back to the start 93 of the sequence of steps and functions 91 and the process is carried out again with the checking time interval for determining the operating situation that indicates an accumulation of secretion. The process also jumps back to the start 93 of the sequence of steps and functions 91 in the case in which the predefined value 123 was not exceeded by the number of counted cough events 117 during the checking time interval 112 and the process is carried out again with the checking time interval for determining the operating situation that indicates an accumulation of secretion.

As is indicated in this FIG. 2 by means of broken lines and as can be seen in FIG. 1, the control signal 131 may be used and processed further during the operation of the ventilator 1 (FIG. 1) preferably for outputting an information message or error message, for example, in text form or in graphic form 44, in the form of an acoustic alarm 42 or of a visual alarm 41.

While specific embodiments of the invention have been shown and described in detail to illustrate the application of the principles of the invention, it will be understood that the invention may be embodied otherwise without departing from such principles.

APPENDIX

List of Reference Designations

1 Medical device, ventilator, system of medical devices
3 Patient
5 Patient gas supply line
7 Inhalation branch of the patient gas supply line
9 Exhalation branch of the patient gas supply line
11 Measuring site for the patient flow rate, Y-piece, connection component
13 Measuring site for the patient pressure, airway pressure
15 Measuring site for the inspiratory flow rate
17 Measuring site for the expiratory flow rate
19 Inspiratory pressure, measuring site
21 Expiratory pressure, measuring site
23 Gas-mixing and -dispensing unit
25 Dispensing valve device
26 Exhalation valve
26' Actuating signal for the expiratory valve 26
27 Control unit, electronic control unit 29 Processor unit
31 Memory unit
40 Alarm generation unit, alarm output
41 Optical signal generation component
42 Acoustic signal generation component
43 Input unit
44 Output unit for text output, display screen
63, 67, 69 Signal/data lines of the pressure-measuring sites
83, 87, 89 Signal/data lines of the flow-measuring sites
91 Sequence of steps and functions
93 Beginning, start
95 Ventilation operation, overall function
97 Flow measured values from the ventilation operation
99 Pressure measured values from the ventilation operation
101 Measured value analysis
103 Patient flow analysis
104 Pressure threshold value
105 Elevation of the airway pressure ($P_{AW}$)
108 Flow threshold value
109 Case distinction (cause of pressure elevation)
111 Case distinction (condition for cough event counting)
112 Checking time interval
113 Initial cough event
115 Event mark (SET)
115' Mark (RESET) of time measurement
117 Counter for cough events
123 Predefined number of cough events during time interval 112
129 Case distinction (frequency of cough events)
131 Control signal
150 Components arranged outside the device
160 Components arranged inside the device

What is claimed is:

1. A method for determining medical operating situations, the method comprising the steps of:
providing a medical device configured for processing sensor signals, which sensor signals are provided by sensors wherein the sensor signals indicate pneumatic/fluidic physical states of a breathing gas in a patient gas-carrying connection system connected and coupled with the medical device for carrying gas between the medical device and a patient and wherein the medical device is configured for transporting gases from and to the patient, from which values of an airway pressure and of a flow rate as well as of a flow rate in the patient gas-carrying connection system are determined in flow directions belonging to the patient gas-carrying connection system;
with the medical device, detecting pneumatic/fluidic physical states in the patient gas-carrying connection system with the determination of values of the airway pressure and the flow rate;
with the medical device, comparing the determined value of the airway pressure to an airway pressure comparison criterion to determine whether the airway pressure comparison criterion is exceeded by the determined value of the airway pressure;
with the medical device, determining a flow direction and whether the medical device is in an operating state in which a smaller quantity of breathing gas is fed by the medical device to the patient than flows away from the patient
with the medical device, determining whether the determined value of the flow rate with the determined flow direction of flow exceeds a flow rate comparison criterion indicating a flow rate with the determined flow direction;
with the medical device, checking to determine whether a cough event or a plurality of cough events has/have occurred;
upon detecting that a cough event or a plurality of cough events has/have occurred with the medical device, with the medical device, initializing a checking time interval and beginning of a detection, counting and recording of a number of cough events during the checking time interval if the medical device is currently in an operating state in which a smaller quantity of breathing gas is fed by the medical device to the patient than flows away from the patient and if the airway pressure comparison criterion is exceeded by the determined value of the airway pressure; and
if at least one cough event has occurred during the checking time interval and if the medical device is currently in the operating state in which a smaller quantity of breathing gas is fed by the medical device to the patient than flows away from the patient and if the airway pressure comparison criterion is exceeded by the determined value of the airway pressure, with the medical device, comparing the number of cough events detected during the checking time interval with a predefined comparison number, with the medical device, determining, on the basis of the comparison of the detected number of cough events to the predefined comparison number, whether an operating situation that indicates an accumulation of fluid is present, and with the medical device, providing a control signal that indicates the determination of the operating situation which indicates an accumulation of fluid is present.

2. A method in accordance with claim 1, wherein a predefined pressure threshold value of about 30 hPa+3 hPa, for an adult patient, is selected as the airway pressure comparison criterion.

3. A method in accordance with claim 1, wherein:
the determination of the airway pressure is carried out based on values of at least one pressure sensor, as one of the sensors; and
the at least one pressure sensor is arranged at a patient connection path or at the patient gas-carrying connection system and/or at an inspiratory connection system and/or at an expiratory connection system.

4. A method in accordance with claim 1, wherein:
the determination of the operating state in which a smaller quantity of breathing gas is fed by the medical device to the patient than flows away from the patient is carried out based on values of at least one flow sensor, as one of the sensors; and
the at least one flow sensor is arranged at a patient connection path or at a connection system.

5. A method in accordance with claim 1, wherein:
the medical device has an expiratory valve;
the medical device has a control following a control course;
the control of the medical device provides information concerning a current phase of breathing, a state of the expiratory valve, or an actuating signal for the expiratory valve;
the determination of the operating state in which a smaller quantity of breathing gas is fed by the medical device to the patient than flows away from the patient is based on information from the control course of the control of the medical device concerning the current phase of breathing or information concerning a state of an expiratory valve or an actuating signal for such an expiratory valve.

6. A method in accordance with claim 1, wherein the checking time interval begins and ends after a predefined duration in a range of 5 minutes to 15 minutes.

7. A method in accordance with claim 1, wherein a number of 30 to 300 consecutive breathing cycles is selected as the checking time interval.

8. A method in accordance with claim 1, wherein the number of cough events is counted with:
the predefined comparison number being decremented towards a value of zero; or
a start value incrementing up to the determined comparison number.

9. A method in accordance with claim 1, wherein a number of at least two cough events, occurring in a predefined time period of 0.3 sec to 5 sec, is selected for detecting the cough event in the operating state in which a smaller quantity of breathing air is fed by the medical device to the patient than flows away from the patient.

10. A medical device comprising:
a connection system configured for transporting breathing gas, the connection system comprising an expiratory path configured and intended for removing an expiratory breathing gas from a patient, an inspiratory path configured and intended for feeding an inspiratory breathing gas from the medical device to the patient, a patient connection path configured and intended for feeding the inspiratory breathing gas from the medical device to the patient and to remove the expiratory of breathing gas from the patient, wherein the expiratory path and the inspiratory path are connected to one another and to the patient connection path by a connection component;
an expiratory valve;
a control unit connected to the expiratory valve for controlling the expiratory valve with an actuating signal following a control course of ventilation;
a pressure-measuring unit comprising at least one pressure sensor arranged in or at the medical device or the connection system and configured and intended for detecting a measured pressure value of a pressure, which is prevailing in the connection system, and wherein the pressure-measuring unit is configured to provide the measured pressure value to the control unit as an airway pressure;
a flow-measuring unit comprising at least one flow sensor arranged in or at the connection system or in or at the medical device and configured and intended for detecting at least one flow rate measured value of a quantity of breathing gas and a flow direction of the breathing gas, which flow direction is associated to the flow rate measured value, which said quantity of the breathing gas flows away from the patient in the connection system or flows from the medical device towards the patient, and wherein the flow-measuring unit is configured to provide this at least one flow rate measured value and the corresponding flow direction to the control unit; and
an alarm generation unit, wherein:
the control unit is configured to determine or input the measured pressure value;
the control unit is configured to determine a current airway pressure on the basis of the at least one measured pressure value;
the control unit is configured to compare the determined values of the airway pressure to an airway pressure comparison criterion to determine whether the airway pressure comparison criterion is exceeded by the determined value of the airway pressure;
the control unit is configured to determine or input at least one flow measured value;
the control unit is configured to determine whether the medical device is in an operating state in which a smaller quantity of breathing air is fed by the medical device to the patient than flows away from the patient based on the control course of ventilation and/or a state of the expiratory valve or the actuating signal for the expiratory valve, and/or based on a comparison of the at least one flow rate measured value and the corresponding flow direction to a flow rate comparison criterion indicating a flow rate and a flow direction, to determine whether the determined value of the flow rate and by the determined flow direction exceeds the flow rate comparison criterion;
the control unit is configured to check whether a cough event or a plurality of cough events has/have occurred;
the control unit is configured to initialize a checking time interval and begin a detection of cough events, counting of a number of cough events and recording of the number of cough events if the medical device is currently in the operating state in which a smaller quantity of breathing air is fed by the medical device to the patient than flows away from the patient, and the airway pressure comparison criterion is exceeded by the determined value of the airway pressure;
the control unit is configured to continue the detection of cough events, counting of the number of cough events and recording of the number of cough events if at least one cough event has occurred during the checking time interval and if the medical device is currently in the operating state in which a smaller quantity of breathing gas is fed by the medical device to the patient than flows away from the patient and if the comparison criterion indicating the airway pressure is exceeded by the currently determined value of the airway pressure;
the control unit is configured to compare the number of cough events detected during the checking time interval with a predefined comparison number;
the control unit is configured to determine, based on the comparison concerning the detected number of cough events in relation to the predefined comparison number, an operating situation that indicates an accumulation of secretion is present; and
the control unit is configured to provide a control signal which indicates the determination of the operating situation that indicates the accumulation of secretion is present.

11. A medical device in accordance with claim 10, wherein:
the at least one pressure sensor for detecting the pressure is arranged and configured at the patient connection path or at the connection component; and
the at least one pressure sensor is configured for a signal transmission, of a value that indicates the airway pressure, to the control unit.

12. A medical device in accordance with claim 10, wherein:
the at least one flow sensor is arranged and configured for detecting flow rates at one or more of:
the patient connection path;
the connection system;
the inspiratory path;
the expiratory path; and the at least one flow sensor is configured for a signal transmission of a value that indicates the airway pressure to the control unit.

13. A medical device in accordance with claim 12, wherein the control unit is configured to determine whether the medical device is in an operating state in which a smaller quantity of breathing gas is fed by the medical device to the patient than flows away from the patient based on a difference from signals of the flow sensor arranged in or at the expiratory path of the connection system and of the flow sensor arranged in or at the inspiratory path of the connection system.

14. A medical device in accordance with claim 10, wherein the alarm generation unit is configured for outputting a message or a notice and/or for a generation of a visual and/or an acoustic warning or an alarm indicating the determination of the operating situation that indicates the accumulation of secretion is present.

15. A medical device in accordance with claim 10, wherein a predefined pressure threshold value of 30 hPa±3 hPa for an adult patient, is selected by the control unit as the airway pressure comparison criterion for the airway pressure.

16. A medical device in accordance with claim 10, wherein the checking time interval is selected by the control unit such that the checking time interval begins and ends after a predefined duration in a time range of 5 minutes to 15 minutes.

17. A medical device in accordance with claim 10, wherein a number of 30 to 300 consecutive breathing cycles is selected by the control unit for the checking time interval.

18. A medical device in accordance with claim 10, wherein the counting of the number of cough events is carried out by the control unit, by incrementing up to the predefined comparison number or decrementing, beginning with the predefined comparison number, towards a value of zero.

19. A medical device in accordance with claim 10, wherein a number of at least two cough events occurring in a predefined time interval is selected by the control unit for detecting the cough event in the operating state in which a smaller quantity of breathing gas is fed by the medical device to the patient than flows away from the patient.

20. A mechanical ventilation medical device comprising:
a gas dispensing unit;
an expiratory valve;
a connection system configured for transporting breathing gas, the connection system comprising an expiratory path connected to the expiratory valve and configured and intended for removing an expiratory breathing gas from a patient, an inspiratory path connected to the gas dispensing unit and configured and intended for feeding an inspiratory breathing gas from the gas dispensing unit to the patient, a patient connection path configured and intended for feeding the inspiratory breathing gas from the inspiratory path to the patient and to remove the expiratory breathing gas from the patient to the expiratory path, wherein the expiratory path and the inspiratory path are connected to one another and to the patient connection path by a connection component;
a control unit connected to the gas dispensing unit for controlling a gas dispensing by the gas dispensing unit and connected to the expiratory valve for controlling the expiratory valve with an actuating signal following a control course of ventilation;
a pressure-measuring unit comprising at least one pressure sensor arranged in or at the medical device or the connection system and configured and intended for detecting a measured pressure value of a pressure, which is prevailing in the connection system, and wherein the pressure-measuring unit is configured to provide the measured pressure value to the control unit as an airway pressure;
a flow-measuring unit comprising at least one flow sensor arranged in or at the connection system or in or at the medical device and configured and intended for detecting at least one flow rate measured value of a quantity of breathing gas and a flow direction of the breathing gas, which flow direction is associated to the flow rate measured value, which said quantity of the breathing gas flows away from the patient in the connection system or flows from the medical device towards the patient, and wherein the flow-measuring unit is configured to provide this at least one flow rate measured value and the corresponding flow direction to the control unit; and
an alarm generation unit, wherein:
the control unit is configured to determine or input the measured pressure value;
the control unit is configured to determine a current airway pressure on the basis of the at least one measured pressure value;
the control unit is configured to compare the determined values of the airway pressure to an airway pressure comparison criterion to determine whether the airway pressure comparison criterion is exceeded by the determined value of the airway pressure;
the control unit is configured to determine or input at least one flow measured value;
the control unit is configured to determine whether the medical device is in an operating state in which a smaller quantity of breathing air is fed by the gas dispensing unit to the patient than flows away from the patient based on the control course of ventilation and/or a state of the expiratory valve or the actuating signal for the expiratory valve, and/or based on a comparison of the at least one flow rate measured value and the corresponding flow direction to a flow rate comparison criterion indicating a flow rate and a flow direction, to determine whether the determined value of the flow rate and by the determined flow direction exceeds the flow rate comparison criterion;
the control unit is configured to check whether a cough event or a plurality of cough events has/have occurred;
the control unit is configured to initialize a checking time interval and begin a detection of cough events, counting of a number of cough events and recording of the number of cough events if the medical device is currently in the operating state in which a smaller quantity of breathing air is fed by the medical device to the patient than flows away from the patient, and the airway pressure comparison criterion is exceeded by the determined value of the airway pressure;
the control unit is configured to continue the detection of cough events, counting of the number of cough events and recording of the number of cough events if at least one cough event has occurred during the checking time interval and if the medical device is currently in the operating state in which a smaller quantity of breathing gas is fed by the medical device to the patient than flows away from the patient and if the comparison criterion indicating the airway pressure is exceeded by the currently determined value of the airway pressure;

the control unit is configured to compare the number of cough events detected during the checking time interval with a predefined comparison number;

the control unit is configured to determine, based on the comparison concerning the detected number of cough events in relation to the predefined comparison number, an operating situation that indicates an accumulation of secretion is present; and the control unit is configured to provide an indicator control signal based on the determination of the operating situation that indicates the accumulation of secretion is present.

\* \* \* \* \*